United States Patent [19]

Arai et al.

[11] Patent Number: 4,652,661
[45] Date of Patent: Mar. 24, 1987

[54] ORGANOSILICON COMPOUND AND PROCESS FOR PREPARING THE SAME

[75] Inventors: Masatoshi Arai; Takeo Inoue; Shinichi Sato, all of Annaka, Japan

[73] Assignee: Shin-Etsu Chemical Co., Ltd., Tokyo, Japan

[21] Appl. No.: 848,147

[22] Filed: Apr. 4, 1986

[30] Foreign Application Priority Data

Apr. 5, 1985 [JP] Japan .................................. 60-071255

[51] Int. Cl.⁴ .......................... C07F 7/08; C07F 7/18; C07D 303/02
[52] U.S. Cl. ...................................... 549/214; 556/440
[58] Field of Search .......................... 556/440; 549/214

[56] References Cited

U.S. PATENT DOCUMENTS

| | | | |
|---|---|---|---|
| 4,304,920 | 12/1981 | Arai et al. | 556/440 |
| 4,314,068 | 2/1982 | Novicky | 556/440 |
| 4,387,240 | 6/1983 | Berg | 556/440 |
| 4,575,545 | 3/1986 | Nakos et al. | 556/440 X |
| 4,575,546 | 3/1986 | Klemarczyk et al. | 556/440 X |

*Primary Examiner*—Paul F. Shaver
*Attorney, Agent, or Firm*—Oblon, Fisher, Spivak, McClelland & Maier

[57] ABSTRACT

A novel carbon functional organosilicon compound represented by the general formula:

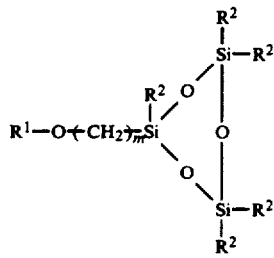

wherein $R^1$ represents a group represented by the formula:

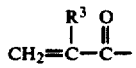

wherein $R^3$ represents a hydrogen atom or a methyl group, or a group represented by the formula:

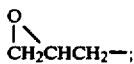

$R^2$, which may be the same or different, each represent a substituted or unsubstituted univalent $C_1$ to $C_8$ hydrocarbon group; and m is an integer of from 2 to 5. This carbon functional compound can easily cause crosslinking reaction on heating, for instance, without forming any by-product. It is useful as a material for modification of acrylic or methacrylic resin, epoxy resin or the like.

5 Claims, 2 Drawing Figures

ORGANOSILICON COMPOUND AND PROCESS FOR PREPARING THE SAME

BACKGROUND OF THE INVENTION

1. Field of the Invention

The present invention relates to a novel carbon functional organosilicon compound.

2. Description of the Prior Art

Hitherto, as a crosslinkable carbon functional siloxane compound, there has been known a siloxane compound which has hydrolyzable groups such as alkoxyl groups in addition to carbon functional groups such as acryloyl, methacryloyl, or glycidyl group. The use of such a siloxane compound as a raw material for a curable composition utilizes hydrolysis of the hydrolyzable groups in the presence of a hydrolysis catalyst followed by crosslinking reaction.

However, in the abovementioned crosslinking reaction, volatile by-products such as alcohols are formed, leading to lowering in the physical properties of the cured product obtained or causing environmental pollution.

SUMMARY OF THE INVENTION

Accordingly, an object of the present invention is to provide a novel carbon functional organosilicon compound which can easily cause crosslinking reaction on heating, for instance, without forming any by-products.

The present invention provides a novel organosilicon compound represented by the general formula (I):

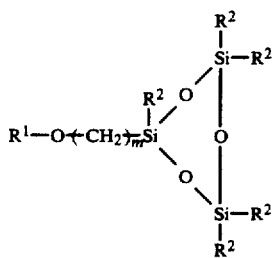
(I)

wherein $R^1$ represents a group represented by the formula:

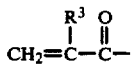

wherein $R^3$ represents a hydrogen atom or a methyl group, or a group represented by the formula:

$R^2$, which may be the same or different, each represent a substituted or unsubstituted univalent $C_1$ to $C_8$ hydrocarbon group; and m is an integer of from 2 to 5.

The carbon functional organosilicon compounds represented by the general formula (I) of the present invention can easily cause crosslinking reaction on heating, for instance, without forming any by-products, and can therefore be used as a raw material for curable compositions which has no fear of undesirable effects by by-products on the physical properties of the cured products obtained and of environmental pollution.

DETAILED DESCRIPTION OF THE INVENTION

Figure 1:
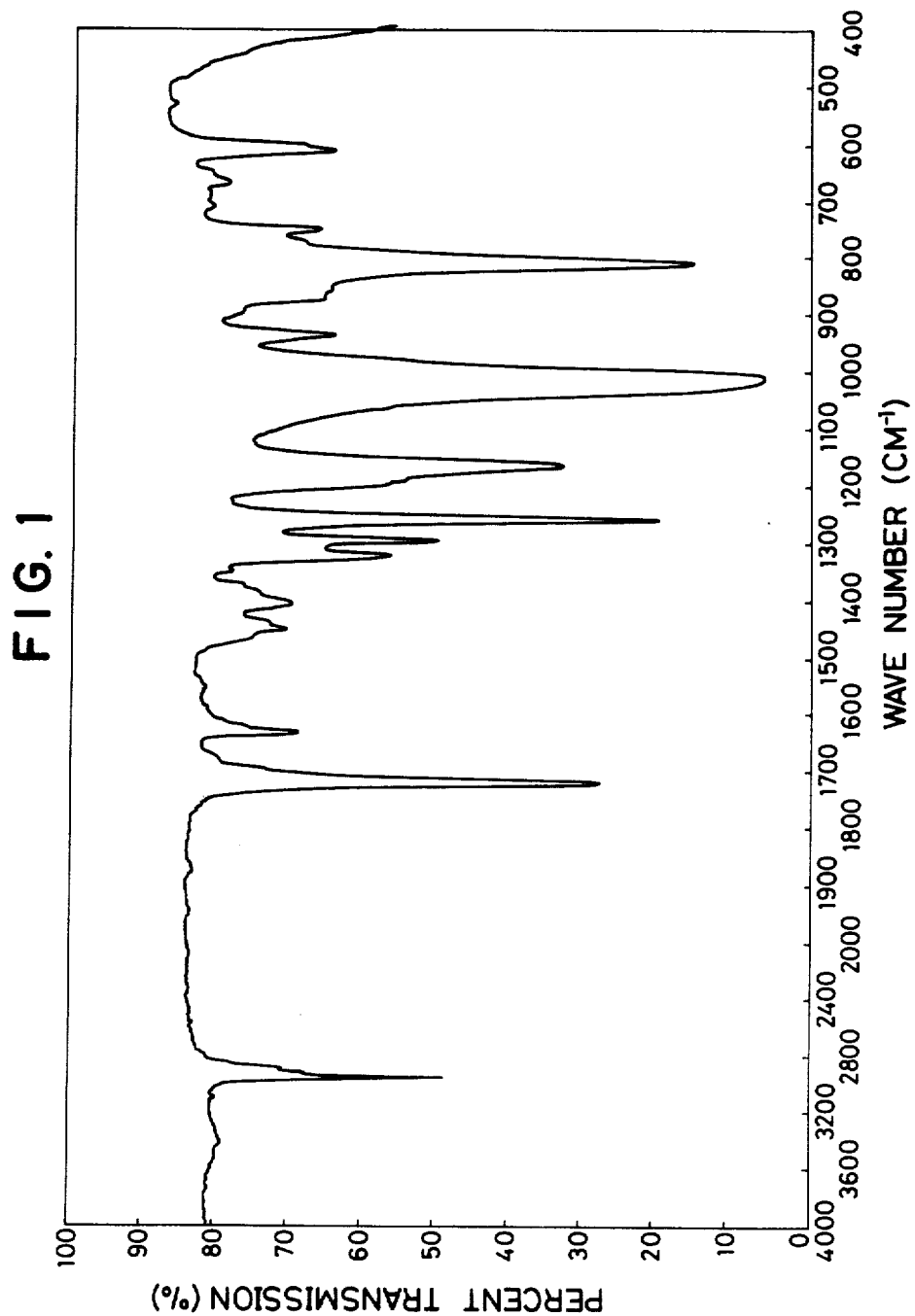
FIG. 1 shows an IR absorption spectrum of an organosilicon compound of this invention obtained in Example 1.

In the general formula (I) representing the organosilicon compounds according to this invention, the substituted or unsubstituted univalent $C_1$ to $C_8$ hydrocarbon groups represented by $R^2$ include, for example, $C_1$ to $C_8$ alkyl groups such as methyl, ethyl, propyl, butyl and the like, $C_1$ to $C_8$ alkenyl groups such as vinyl, allyl and the like, $C_6$ to $C_8$ aryl groups such as phenyl, tolyl and the like, $C_7$ to $C_8$ aralkyl groups such as benzyl and the like and these groups in which part of the hydrogen atoms therein are substituted by halogen atoms, cyano groups or the like. Of these groups, typical examples are $C_1$ to $C_3$ alkyl groups, vinyl group, phenyl group, γ-trifluoropropyl group and the like in view of favorable availability of the starting compounds to be used in the preparation of the organosilicon compounds.

The organosilicon compounds of the general formula (I) can be easily prepared by subjecting a compound represented by the general formula (II):

(II)

wherein $R^1$ is an defined in the general formula (I), and n is an integer of from 0 to 3, and a cyclotrisiloxane compound represented by the general formula (III):

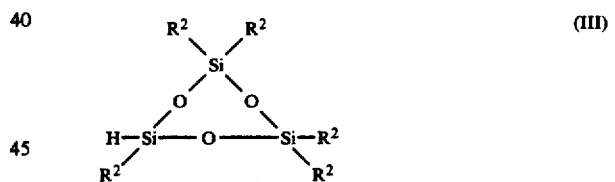
(III)

wherein $R^2$ is as defined in the general formula (I), to addition reaction of the compound of the general formula (III) to the compound of the general formula (ii) in the presence of a Group VIII metal catalyst.

The processes of preparing the compounds of general formula (II) is apparent to those skilled in the art. Some of the compounds are commercially available.

The compounds of the general formula (III) can be prepared, for example, by reacting a dichloromonoorganosilane ($R^2HSiCl_2$) and a tetraorganodisiloxane-1,3-diol ($HOSi(R^2)_2OSi(R^2)_2OH$) in the presence of triethylamine in diethyl ether, or by the process disclosed in Japanese Laid-open Patent Publication No. 115592/1985.

The Group VIII metal catalysts used in the addition reaction include Group VIII metals and compounds containing the same, of which preferred is a platinum catalyst, for example, chloroplatinic acid, alcoholic solutions of chloroplatinic acid, chloroplatinic acid modified by vinylsiloxane, platinum black, complexes of chloroplatinic acid with an olefin or an aldehyde and the like. The catalyst is suitably used in an amount of from 5 to 50 ppm, as metal, based on the total amount of the raction mixture.

The above addition reaction is generally carried out in an organic solvent. Preferred organic solvents include, for example, aromatic hydrocarbons such as benzene, toluene, xylene and the like. The reaction temperature is suitably about 50° to 150° C., preferably 80° to 140° C.

The cyclotrisiloxane ring contained in the organosilicon compound of the invention readily opens on heating, for instance, due to its internal stress, thereby causing polymerization. The ring opening polymerization of the organosilicon compound in the presence of a suitable catalyst such as a tin compound produces an organopolysiloxane having pendent carbon functional groups such as acryloyl, methacryloyl or glycidyl group. Such organopolysiloxanes are useful, for example, as a modifying material for improvement of cold resistance, heat resistance, weathering resistance, etc. of arcylic or methacrylic resins and epoxy resins. The organosilicon compound of the invention can be also useful as a starting monomer for preparation of acrylic or methacrylic resins and epoxy resins for improvement of the characteristics as mentioned above of the resins.

The present invention will now be described more specifically below with reference to examples, which do not limit the scope of the invention.

EXAMPLES

EXAMPLE 1

A reaction vessel is charged with 15.8 g (0.125 mole) of allyl methacrylate, 0.07 g of an isopropanol solution of chloroplatinic acid (Pt content: 1.0% by weight) and 0.07 g of butylated hydroxytoluene, and while heating the resulting mixture at 65° C., 20.8 g (0.1 mole) of pentamethylcyclotrisiloxane was added dropwise to the mixture over about one hour. Thereafter, a reaction was carried out for another one hour at 80° C. Then, the reaction mixture was subjected to distillation under a reduced pressure to obtain 22.1 g of a liquid product having a boiling point of 111° C. (at 4 mmHg). By the analytical data set forth below, the liquid product was identified as the organosilicon compound having the following structure:

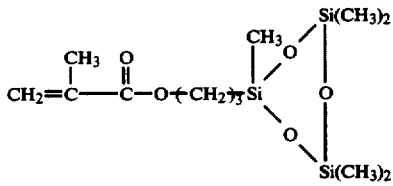

Elemental analysis:

|  | C | H | Si |
|---|---|---|---|
| Calcd. (%) (for Si$_3$C$_{12}$H$_{26}$O$_5$): | 43.11 | 7.78 | 25.15 |
| Found (%): | 43.00 | 7.81 | 25.21 |

Molecular weight (gas mass spectroscopy): 334
Refractive index (25° C.): 1.4271
IR absorption spectrum (neat): shown in FIG. 1

EXAMPLE 2

The same procedure was repeated as in Example 1 except for using 14.3 g (0.125 mole) of allyl glycidyl ether in place of allyl methacrylate to obtain 22.6 g of a liquid product having a boiling point of 110° C. (at 3 mmHg). By the analytical data set forth below, the product was identified as the organosilicon compound having the following structure:

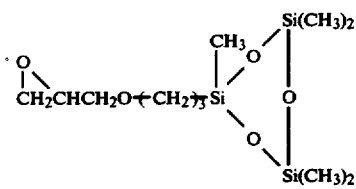

Elemental analysis:

|  | C | H | O |
|---|---|---|---|
| Calcd. (%) (for Si$_3$C$_{11}$H$_{26}$O$_5$): | 40.99 | 8.07 | 26.09 |
| Found (%): | 41.03 | 8.11 | 26.21 |

Figure 2:
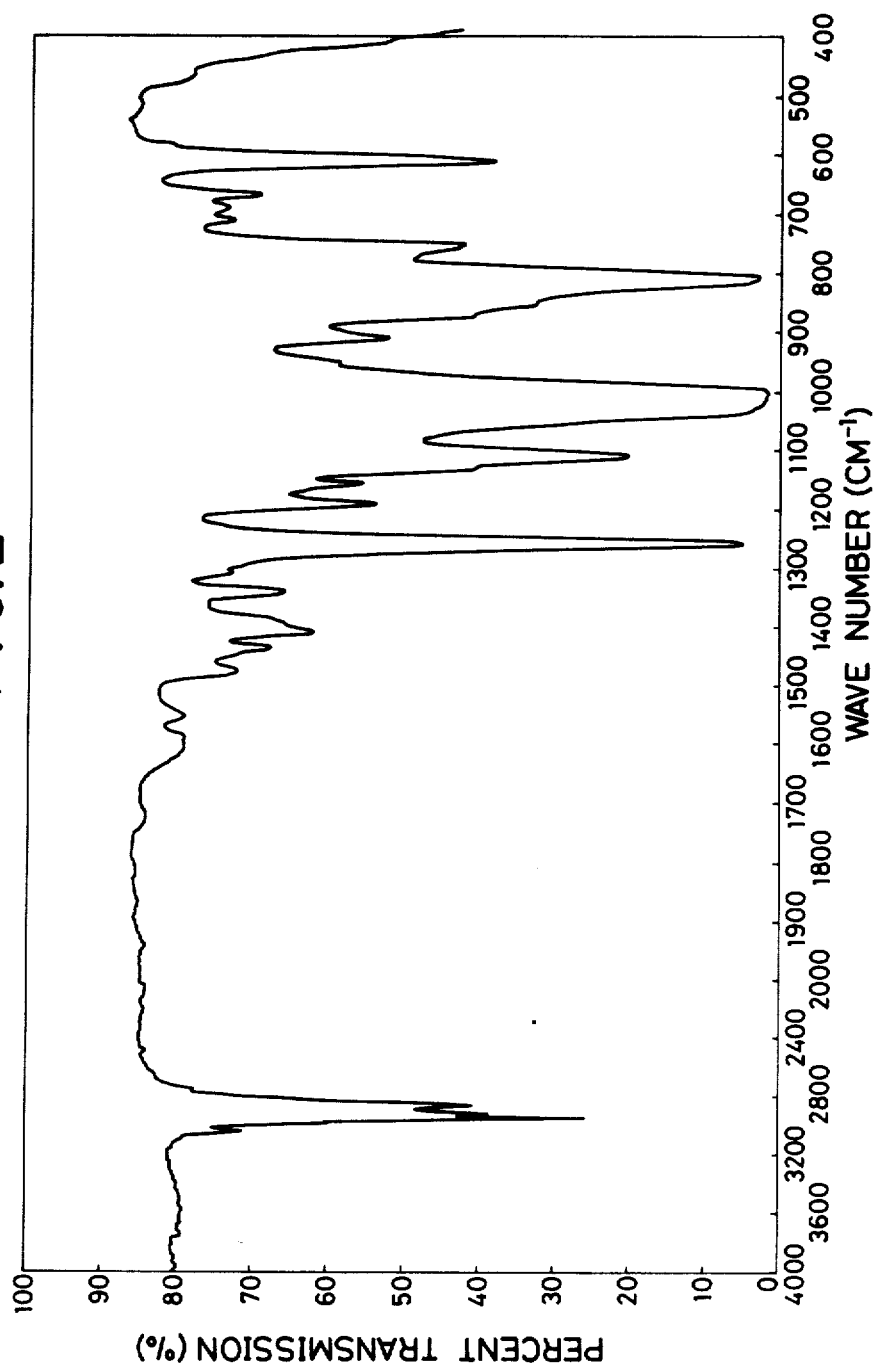
FIG. 2 shows an IR absorption spectrum of an organosilicon compound of this invention obtained in Example 2.

Molecular weight (gas mass spectroscopy): 322
Refractive index (25° C.): 1.4262
IR absorption spectrum (neat): shown in FIG. 2

We claim:

1. An organosilicon compound represented by the general formula (I)

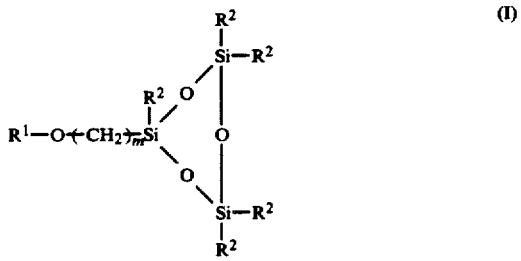

(I)

wherein R$^1$ represents a group represented by the formula:

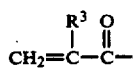

wherein R$^3$ represents a hydrogen atom or a methyl group, or a group represented by the formula:

R$^2$, which may be the same or different, each represent a substituted or unsubstituted univalent C$_1$ to C$_8$ hydrocarbon group; and m is an integer of from 2 to 5.

2. The compound according to claim 1, wherein R$^1$ is methacryloyl group, and R$^2$ is methyl group.

3. The compounds according to claim 1, wherein R$^1$ is the group represented by the formula:

and $R^2$ is methyl group.

4. A process for preparing an organosilicon compound of the general formula (I) described above, comprising subjecting a compound represented by the general formula (II):

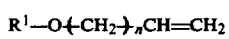 (II)

wherein $R^1$ is as defined in the general formula (I), and n is an integer of from 0 to 3, and a cyclotrisiloxane compound represented by the general formula (III):

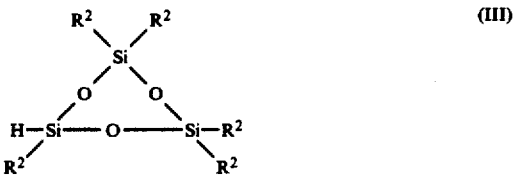 (III)

wherein $R^2$ is as defined in the general formula (I), to an addition reaction in the presence of a Group VIII metal catalyst.

5. The process according to claim 4, wherein said catalyst is a platinum catalyst.

* * * * *